United States Patent [19]

Bollenbacher

[11] 4,159,332

[45] Jun. 26, 1979

[54] PREVENTION OF OR REDUCTION IN SEVERITY OF MYOCARDIAL INFARCTION

[75] Inventor: Paul V. Bollenbacher, New Hope, Pa.

[73] Assignee: Unimed, Inc., Somerville, N.J.

[21] Appl. No.: 852,984

[22] Filed: Nov. 18, 1977

Related U.S. Application Data

[63] Continuation-in-part of Ser. No. 690,952, May 28, 1976, abandoned.

[51] Int. Cl.² ............................................. A61K 31/44
[52] U.S. Cl. .................................................... 424/263
[58] Field of Search ......................................... 424/263

[56] References Cited

PUBLICATIONS

Chemical Abstracts 67:67557p (1967).
Chemical Abstracts 79:38512n (1973).

Primary Examiner—Jerome D. Goldberg
Attorney, Agent, or Firm—Steinberg & Blake

[57] ABSTRACT

Myocardial infarction is prevented entirely or its severity is reduced in patients subject to the same by administering to such patients after occurrence of coronary occlusion and prior to the setting in of the myocardial infarction of a myocardial infarction preventing effective amount of a beta-(2- or 4-pyridyl-alkyl)-amine or a non-toxic acid addition salt thereof. Such administration acts to help prevent the onset of the myocardial infarction or acts to reduce the size of any formed infarct.

4 Claims, No Drawings

PREVENTION OF OR REDUCTION IN SEVERITY OF MYOCARDIAL INFARCTION

CROSS REFERENCE TO RELATED APPLICATION

This invention is a continuation-in-part of my co-pending application Ser. No. 690,952, filed May 28, 1976, for "PREVENTION OF MYOCARDIAL INFARCTION", now abandoned.

BACKGROUND OF THE INVENTION

Since atherosclerotic coronary heart disease is the single greatest cause of death in the United States, the need to provide a means to prevent myocardial infarction or to at least reduce the size of any infarct after a coronary occlusion occurs has resulted in considerable investigation. Attempts to increase the supply of blood to the heart by means of a coronary vasodilator in order to prevent the onset of myocardial infarction have not only been unsuccessful but have actually been found to be contraindicated. Thus, it has been found that the administration of the common vasodilators such as nitroglycerin after the occurrence of a coronary occlusion causes increased work of the heart, edema and an increase in blood pressure, all of which result in a worsening of the subsequent myocardial infarction.

As a consequence, present medical practice in the case of the occurrence of a coronary occlusion is to simply have the patient rest, to treat the pain, for example with morphine, and sometimes to administer a vasopressor, namely dopamine. No drug treatment has been established to prevent or reduce the size of myocardial infarction.

SUMMARY OF THE INVENTION

Generally speaking, in accordance with the present invention, there is administered to a patient subject to myocardial infarction a myocardial infarction preventing amount of a beta-(2- or 4-pyridyl-alkyl)-amine or a non-toxic acid addition salt thereof, the administration occurring after the coronary occlusion and prior to onsert of the myocardial infarction.

It is accordingly a primary object of the present invention to provide a treatment which helps to prevent myocardial infarction or to reduce the severity of any infarction.

While the manner in which the beta-(2- or 4-pyridyl-alkyl)-amine acts to prevent the myocardial infarction is not known, it has been confirmed that either the infarct is prevented or the size reduced by the use of the drug in accordance with the present invention.

It is still another object of the present invention to provide for the administration of beta-(2- or 4-pyridyl-alkyl)-amines in order to reduce probability of a patient suffering from myocardial infarction.

Other objects and advantages of the present invention will be apparent from a further reading of the specification and of the appended claims.

While the invention is in general applicable to the beta-(2- or 4-pyridyl-loweralkyl) amines and their non-toxic acid addition salts such as the hydrochloride, fumarate, sulphate, gluconate, etc., reference herein will generally be made with respect to the product generally known as betahistine-HCl which is the compound 2-(2-methylamino) ethyl pyridine dihydrochloride.

The beta-(2- or 4-pyridyl-alkyl)-amines are preferably administered for the purposes of the present invention in an amount of about 2–50 mg per day, preferably in an amount of about 4–45 mg per day, and most preferably in an amount of about 12–45 mg per day. To best prevent the onset of the myocardial infarction, the administration is by intravenous infusion commenced as soon as possible after the occurrence of the coronary occlusion. After a few days the intravenous infusion is stopped. Further administration may be continued in a unit dosage of about 2–15 mg per day administered 3–4 times a day. The compounds may be administered either orally or by injection.

Although the invention is applicable to all of the 2- or 4-pyridyl alkyl amines mentioned above, as well as other pyridyl alkyl amines and pyridyl alkyl amine addition salts such as 2-(2'-(N,N-diethylamino) ethyl) pyridine monofumarate; 2-(2'(N-ethylamino) ethyl) pyridine monofumarate; 2-(2'(amino) ethyl) pyridine monofumarate; 4-(2'-(amino) ethyl) pyridine monofumarate; 4-(2'-(methylamino) ethyl) pyridine monofumarate; beta-(2-pyridyl)-ethyldiethylamine hydrochloride; 1-(2-pyridyl)-2-methylaminopropane hydrochloride; and beta-(2-pyridyl)-ethylamine hydrochloride, the discussion herein generally will be made with respect to betahistine hydrochloride.

Tests were carried out to evaluate the effectiveness of betahistine-HCl in preventing myocardial infarction and these tests determine the effectiveness in prevention of surgically induced myocardial infarction.

Tests were carried out on dogs, different groups of dogs being given the betahistine-HCl at different times after surgical ligation and some of the dogs being used as controls were given saline instead of the betahistine HCl.

The ligations were performed without prior knowledge of which treatment the animals would receive. At the appropriated time after the ligation the animals received a six hour continuous intravenous infusion of betahistine-HCl in saline or saline alone. At the end of the infusion the beating heart was excised and biopsied.

In chronic time costs experiments, all of the animals receiving saline instead of betahistine-HCl developed infarcts. Of the remaining animals, those that received betahistine-HCl were significantly protected from the myocardial infarct. Some of the animals receiving the betahistine-HCl immediately after ligation developed no infarcts at all. The other animals developed infarcts but the infarcts were significantly smaller than in the control animals (those that received saline) and the infarcts were smaller, the earlier that the animal received the drug.

Thus, in acute time course experiment animals receiving betahistine-HCl were less ischemic than the saline control group. The failure of infarction to develop in some of the dogs treated with betahistine-HCl immediately after ligation and the reduction in size of infarcts present in animals treated at various times after ligation confirms the effectiveness of betahistine-HCl in helping to prevent myocardial infarction.

Although the betahistine-HCl may be administered orally or by injection for the purposes of the present invention, it is apparent that the betahistine-HCl should be administered as soon as possible after the occurrence of the coronary occlusion and intravenous infusion is the most effective for this purpose. Administration can be continued subsequently by oral administration.

It is further apparent that the betahistine hydrochloride can be used to treat human patients for the purpose of preventing myocardial infarction by administration thereof to the patient following the occurrence of a coronary occlusion. Such administration should be commenced as soon as possible after the occurrence of the coronary occlusion.

I claim:

1. Method of preventing or reducing the severity of myocardial infarction which comprises administering to a subject of a coronary occlusion after the occurrence of the coronary occlusion and prior to the onset of a myocardial infarction of a myocardial infarction preventing amount of a compound selected from the group consisting of beta-(2-pyridyl loweralkyl mono- or di-loweralkyl)-lower alkyl amines, beta-(4-pyridyl loweralkyl mono- or di-loweralkyl)-lower alkyl amines and non-toxic acid addition salts thereof.

2. Method according to claim 1 wherein said compound is betahistine.

3. Method according to claim 1 wherein said compound is betahistine hydrochloride.

4. Method according to claim 1 wherein said compound is administered by intravenous infusion.